US011581073B2

(12) United States Patent
MacManus et al.

(10) Patent No.: US 11,581,073 B2
(45) Date of Patent: Feb. 14, 2023

(54) DYNAMIC DATABASE UPDATES USING PROBABILISTIC DETERMINATIONS

(71) Applicant: Optum Services (Ireland) Limited, Dublin (IE)

(72) Inventors: Lorcan B. MacManus, Co Kildare (IE); Amy Neftzger, Franklin, TN (US)

(73) Assignee: Optum Services (Ireland) Limited, Dublin (IE)

( * ) Notice: Subject to any disclaimer, the term of this patent is extended or adjusted under 35 U.S.C. 154(b) by 362 days.

(21) Appl. No.: 16/677,990

(22) Filed: Nov. 8, 2019

(65) Prior Publication Data

US 2021/0141834 A1    May 13, 2021

(51) Int. Cl.

| G06F 7/00 | (2006.01) |
|---|---|
| G16H 10/60 | (2018.01) |
| G06F 16/906 | (2019.01) |
| G06N 20/00 | (2019.01) |
| G06F 16/904 | (2019.01) |
| G06F 18/24 | (2023.01) |

(52) U.S. Cl.
CPC ........... *G16H 10/60* (2018.01); *G06F 16/904* (2019.01); *G06F 16/906* (2019.01); *G06F 18/24* (2023.01); *G06N 20/00* (2019.01)

(58) Field of Classification Search
CPC ..... G06F 16/904; G06F 16/906; G06N 20/00; G06K 9/6267
USPC ..................... 707/722, 723, 737
See application file for complete search history.

(56) References Cited

U.S. PATENT DOCUMENTS

| 2007/0282824 | A1 | 12/2007 | Ellingsworth |
|---|---|---|---|
| 2011/0054944 | A1* | 3/2011 | Sandberg ............... G06Q 30/04 |
| | | | 705/3 |
| 2011/0282695 | A1 | 11/2011 | Blue |
| 2013/0006655 | A1 | 1/2013 | Van Arkel et al. |
| 2015/0127370 | A1 | 5/2015 | Cornelis |
| 2017/0132866 | A1* | 5/2017 | Kuklinski ............ G07D 7/2083 |
| 2018/0239870 | A1 | 8/2018 | Goldman et al. |
| 2020/0019767 | A1* | 1/2020 | Porter .................... G06Q 30/04 |
| 2020/0387545 | A1* | 12/2020 | Tripathi ................. G06N 20/00 |

* cited by examiner

*Primary Examiner* — Md I Uddin
(74) *Attorney, Agent, or Firm* — Alston & Bird LLP

(57) ABSTRACT

Methods, apparatus, systems, computing devices, computing entities, and/or the like for using machine-learning concepts (e.g., machine learning models) to determine predicted taxonomy-based classification scores for claims and dynamically update data fields based on the same.

18 Claims, 13 Drawing Sheets

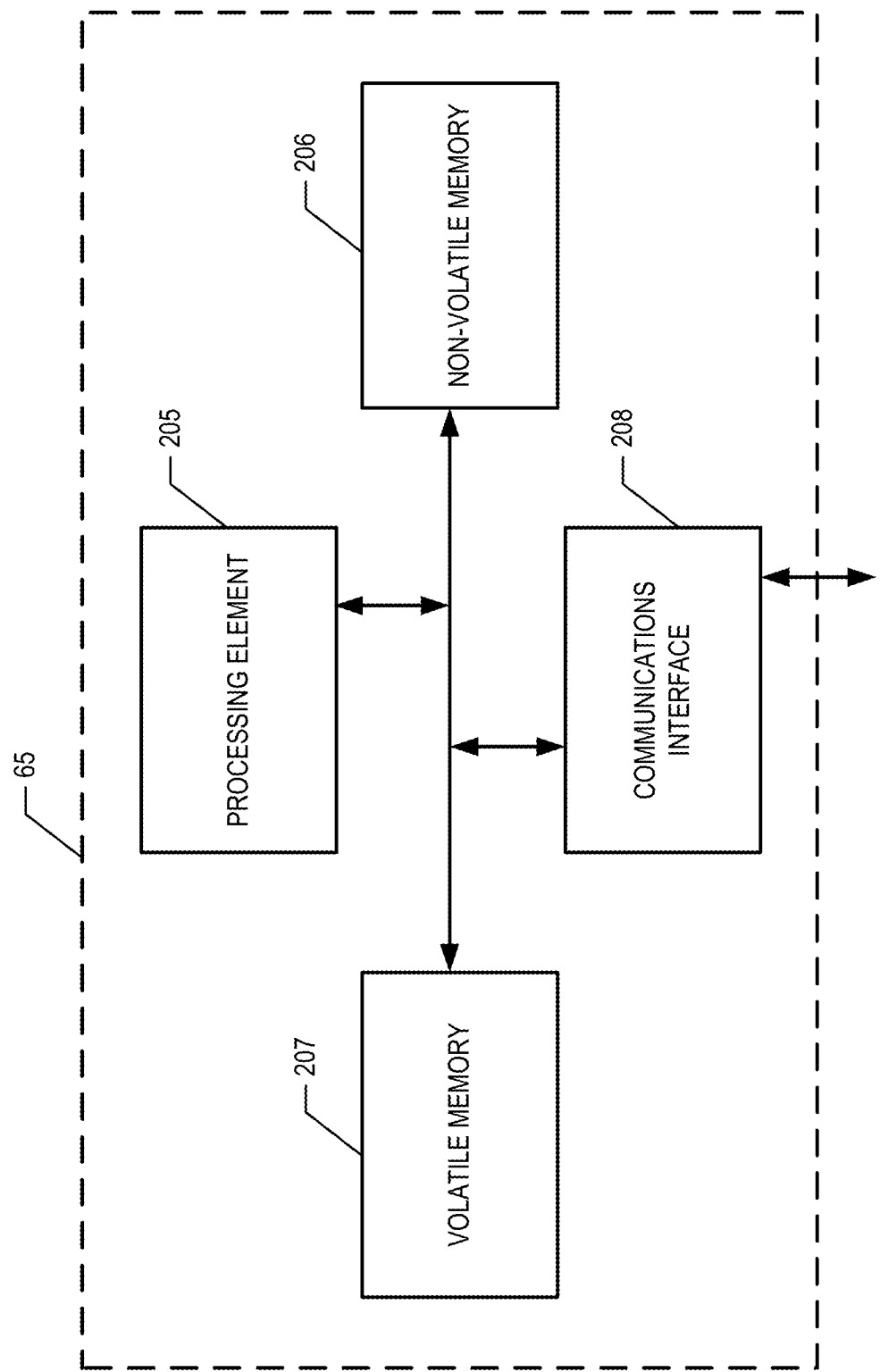

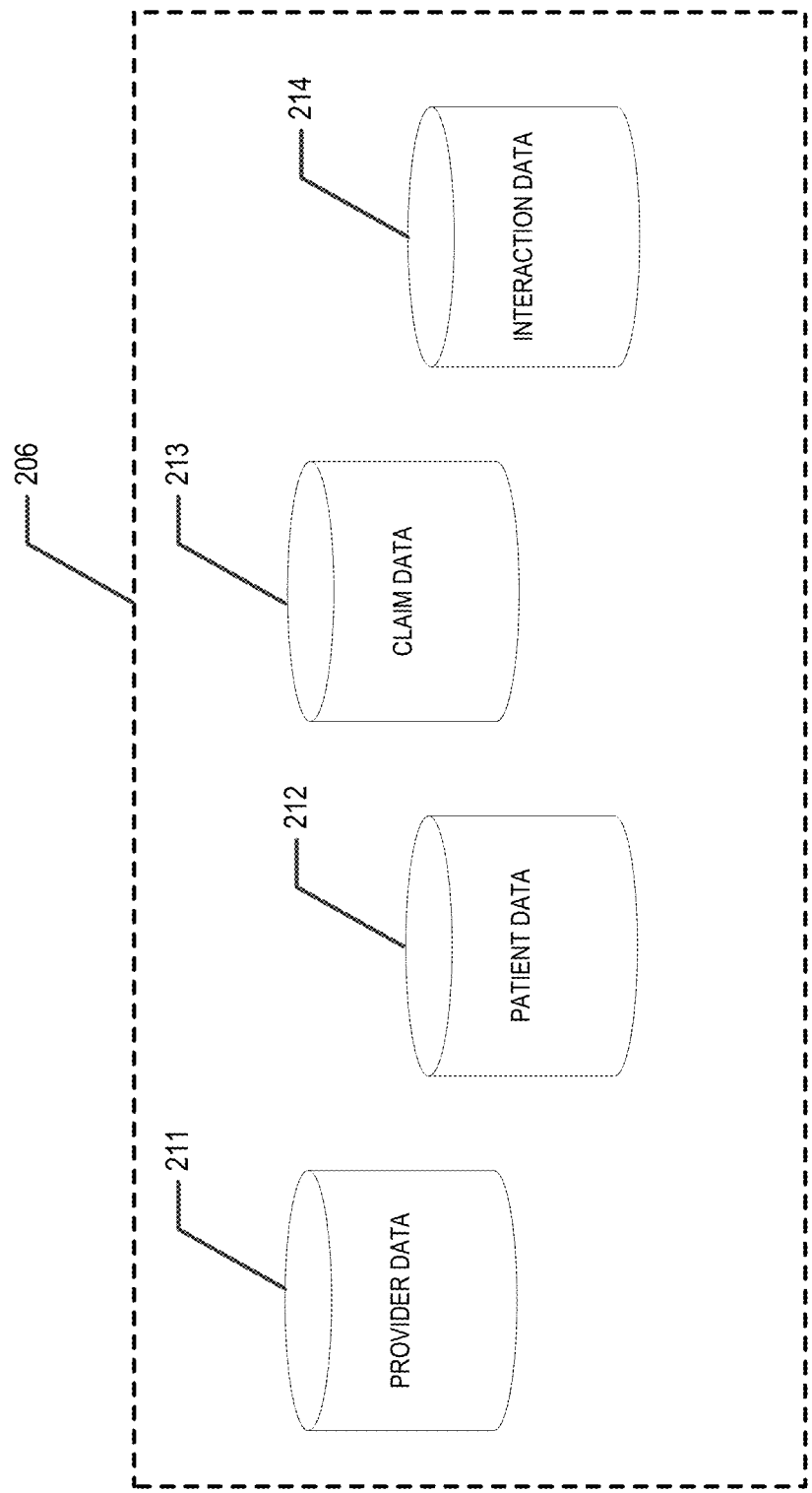

FIG. 4A

| Claim_ID | Date_Service | Pat_ID | Prov_ID | Bill_Code | Prov_Class | Prov_Class_Score | Assign_Queue |
|---|---|---|---|---|---|---|---|
| 12345678 | 2020-10-01T04:32:00 | 10101010 | AAAAAAA | L1900 | DME | | |

FIG. 4B

| Prov_ID | Prov_Name | Prov_Loc | Prov_Contract | Prov_Class |
|---|---|---|---|---|
| AAAAAAA | Dr. A | West | Y | DME |

FIG. 4C

| Claim_ID | Date_Service | Pat_ID | Prov_ID | Bill_Code | Prov_Class | Prov_Class_Score | Assign_Queue |
|---|---|---|---|---|---|---|---|
| 12345678 | 2020-10-01T04:32:00 | 10101010 | 11111111 | L1900 | DME | 0.97 | Bypass |

| Claim_ID | Date_Service | Pat_ID | Prov_ID | Bill_Code | Prov_Class | Prov_Class_Score | Assign_Queue |
|---|---|---|---|---|---|---|---|
| 23456789 | 2020-11-11T08:17:00 | 12121212 | BBBBBBBB | 43590 | AMB | | |

FIG. 4D

| Prov_ID | Prov_Name | Prov_Loc | Prov_Contract | Prov_Class |
|---|---|---|---|---|
| BBBBBBBB | Dr. B | East | Y | SNF |

FIG. 4E

| Claim_ID | Date_Service | Pat_ID | Prov_ID | Bill_Code | Prov_Class | Prov_Class_Score | Assign_Queue |
|---|---|---|---|---|---|---|---|
| 23456789 | 2020-11-11T08:17:00 | 12121212 | BBBBBBBB | 43590 | AMB | 0.63 | Review |

| Claim_ID | Date_Service | Pat_ID | Prov_ID | Bill_Code | Prov_Class | Prov_Class_Score | Assign_Queue |
|---|---|---|---|---|---|---|---|
| 34567891 | 2020-08-09T14:53:00 | 14141414 | CCCCCCC | 99391 | PRI | | |

FIG. 4H

| Prov_ID | Prov_Name | Prov_Loc | Prov_Contract | Prov_Class |
|---|---|---|---|---|
| CCCCCCC | Dr. C | South | Y | |

FIG. 4I

| Claim_ID | Date_Service | Pat_ID | Prov_ID | Bill_Code | Prov_Class | Prov_Class_Score | Assign_Queue |
|---|---|---|---|---|---|---|---|
| 34567891 | 2020-08-09T14:53:00 | 14141414 | CCCCCCC | 99391 | PRI | 0.84 | Standard |

FIG. 4J

| Prov_ID | Prov_Name | Prov_Loc | Prov_Contract | Prov_Class |
|---|---|---|---|---|
| CCCCCCC | Dr. C | South | Y | PRI |

FIG. 6

| | AMB | ASC | DME | ECF | HH | INP | LAB | OUT | PHY | PRI | SNF | SPC | UNK | Error |
|---|---|---|---|---|---|---|---|---|---|---|---|---|---|---|
| AMB | 12,073 | - | 8 | - | - | - | 8 | - | 12 | 95 | - | 75 | 11 | 79.9% |
| ASC | 5,588 | - | - | - | - | - | - | - | - | - | - | - | - | 1.6% |
| DME | 5 | - | 35,223 | - | 89 | 2,380 | 18 | - | 12 | 80 | 1 | 322 | 138 | 9.6% |
| ECF | - | - | - | 33,621 | 6,102 | 29 | - | - | - | - | 5 | - | - | 11.1% |
| HH | 1 | 141 | 167 | - | - | 3 | 4 | - | 14 | 117 | 195 | 213 | 47 | 40.8% |
| INP | - | - | - | 36 | 10 | 424,419 | 114,954 | 22 | - | - | 239 | 21 | 3 | 9.9% |
| LAB | - | - | 26 | - | 1 | - | 125 | 303 | 2 | - | 13 | 4,496 | 39 | 40.8% |
| OUT | 4 | - | 27 | - | - | 20 | 5 | 3 | 1 | - | - | 861 | 33 | 22.5% |
| PHY | 28 | - | 18 | - | 9 | 2 | 19,508 | 123 | 30,204 | 1,190 | - | 462 | 147 | 29.7% |
| PRI | - | - | 139 | 7 | 49 | 861 | 13,469 | 59 | 457 | 142,703 | - | 37,556 | 1,097 | 15.6% |
| SNF | - | - | - | - | - | - | - | - | - | - | 48,310 | - | - | 15.2% |
| SPC | 6 | - | 526 | - | 28 | 2 | 604 | 5 | 2,762 | 28,204 | 1 | 274,642 | 3,989 | 15.2% |
| UNK | 51 | - | 325 | - | 94 | - | - | - | 539 | 3,107 | - | 12,381 | 34,410 | 35.5% |
| Totals | 12,170 | 5,729 | 36,079 | 33,664 | 6,382 | 427,716 | 148,695 | 515 | 34,004 | 183,754 | 48,764 | 330,849 | 39,913 | 11.2% |

DYNAMIC DATABASE UPDATES USING PROBABILISTIC DETERMINATIONS

BACKGROUND

Provider classification is an important topic in relationship management for health insurance companies. Providers cover a diverse range of specializations, from inpatient hospitals to primary care physicians. Inaccurate classification can be due to data entry errors, or more likely, owing to a change in the organizational structure of the provider's business (such as a merger or acquisition of another practice). Since provider taxonomy is not a data field required for payment of claims, very few providers update this information in corresponding systems. As a result, this data field may be unpopulated or incorrect in most systems, and current operational processes do not rely on the information provided, but instead perform manual searches into each individual provider's billing history in order to make a taxonomy-based classification. Thus, the time required for this step may range anywhere from a few hours to several days, depending upon the systems being queried and the number of claims.

Through ingenuity and innovation, various embodiments of the present invention make substantial improvements to the above challenges.

BRIEF SUMMARY

In general, embodiments of the present invention provide methods, apparatus, systems, computing devices, computing entities, and/or the like.

In accordance with one aspect, a method is provided. In one embodiment, the method comprises storing, by one or more processors, (a) a first record for a first provider in a datastore, wherein the first record comprises a data field with a first assigned taxonomy-based classification for the first provider from a taxonomy, (b) a second record for a first provider in the datastore, wherein the second record comprises a data field with a second assigned taxonomy-based classification for the second provider from the taxonomy, and (c) a third record for a third provider in the datastore, wherein the third record comprises a data field with a third assigned taxonomy-based classification for the third provider from the taxonomy; generating, by the one or more processors and one or more machine learning models, (a) for a first claim for the first provider and based at least in part on first claim data, a first plurality of predicted taxonomy-based classification scores for each classification in the taxonomy, (b) for a second claim for the second provider and based at least in part on second claim data, a second plurality of predicted taxonomy-based classification scores for each classification in the taxonomy, and (c) for a third claim for the third provider and based at least in part on third claim data, a third plurality of predicted taxonomy-based classification scores for each classification in the taxonomy; programmatically identifying, by the one or more processors, (a) a first predicted taxonomy-based classification for the first claim from the first plurality of predicted taxonomy-based classification scores, (b) a second predicted taxonomy-based classification for the second claim from the second plurality of predicted taxonomy-based classification scores, and (c) a third predicted taxonomy-based classification for the third claim from the third plurality of predicted taxonomy-based classification scores; programmatically comparing, by the one or more processors, (a) the first predicted taxonomy-based classification for the first provider with the first assigned taxonomy-based classification for the first provider, (b) the second predicted taxonomy-based classification for the second provider with the second assigned taxonomy-based classification for the second provider, (c) the third predicted taxonomy-based classification for the third provider with the third assigned taxonomy-based classification for the third provider; responsive to the respective comparisons, programmatically assigning, by the one or more processors, (a) an unknown condition to the first claim, (b) a match condition to the second claim, and (c) a not matched condition to the third claim; and responsive to assigning the unknown condition to the first claim, programmatically updating the data field of the first record with the first assigned taxonomy-based classification to the first predicted taxonomy-based classification.

In accordance with another aspect, a computer program product is provided. The computer program product may comprise at least one computer-readable storage medium having computer-readable program code portions stored therein, the computer-readable program code portions comprising executable portions configured to store (a) a first record for a first provider in a datastore, wherein the first record comprises a data field with a first assigned taxonomy-based classification for the first provider from a taxonomy, (b) a second record for a first provider in the datastore, wherein the second record comprises a data field with a second assigned taxonomy-based classification for the second provider from the taxonomy, and (c) a third record for a third provider in the datastore, wherein the third record comprises a data field with a third assigned taxonomy-based classification for the third provider from the taxonomy; generate, by one or more machine learning models, (a) for a first claim for the first provider and based at least in part on first claim data, a first plurality of predicted taxonomy-based classification scores for each classification in the taxonomy, (b) for a second claim for the second provider and based at least in part on second claim data, a second plurality of predicted taxonomy-based classification scores for each classification in the taxonomy, and (c) for a third claim for the third provider and based at least in part on third claim data, a third plurality of predicted taxonomy-based classification scores for each classification in the taxonomy; programmatically identify (a) a first predicted taxonomy-based classification for the first claim from the first plurality of predicted taxonomy-based classification scores, (b) a second predicted taxonomy-based classification for the second claim from the second plurality of predicted taxonomy-based classification scores, and (c) a third predicted taxonomy-based classification for the third claim from the third plurality of predicted taxonomy-based classification scores; programmatically compare (a) the first predicted taxonomy-based classification for the first provider with the first assigned taxonomy-based classification for the first provider, (b) the second predicted taxonomy-based classification for the second provider with the second assigned taxonomy-based classification for the second provider, (c) the third predicted taxonomy-based classification for the third provider with the third assigned taxonomy-based classification for the third provider; responsive to the respective comparisons, programmatically assign (a) an unknown condition to the first claim, (b) a match condition to the second claim, and (c) a not matched condition to the third claim; and responsive to assigning the unknown condition to the first claim, programmatically update the data field of the first record with the first assigned taxonomy-based classification to the first predicted taxonomy-based classification.

In accordance with yet another aspect, a computing system comprising at least one processor and at least one memory including computer program code is provided. In one embodiment, the at least one memory and the computer program code may be configured to, with the processor, cause the apparatus to store (a) a first record for a first provider in a datastore, wherein the first record comprises a data field with a first assigned taxonomy-based classification for the first provider from a taxonomy, (b) a second record for a first provider in the datastore, wherein the second record comprises a data field with a second assigned taxonomy-based classification for the second provider from the taxonomy, and (c) a third record for a third provider in the datastore, wherein the third record comprises a data field with a third assigned taxonomy-based classification for the third provider from the taxonomy; generate, by one or more machine learning models, (a) for a first claim for the first provider and based at least in part on first claim data, a first plurality of predicted taxonomy-based classification scores for each classification in the taxonomy, (b) for a second claim for the second provider and based at least in part on second claim data, a second plurality of predicted taxonomy-based classification scores for each classification in the taxonomy, and (c) for a third claim for the third provider and based at least in part on third claim data, a third plurality of predicted taxonomy-based classification scores for each classification in the taxonomy; programmatically identify (a) a first predicted taxonomy-based classification for the first claim from the first plurality of predicted taxonomy-based classification scores, (b) a second predicted taxonomy-based classification for the second claim from the second plurality of predicted taxonomy-based classification scores, and (c) a third predicted taxonomy-based classification for the third claim from the third plurality of predicted taxonomy-based classification scores; programmatically compare (a) the first predicted taxonomy-based classification for the first provider with the first assigned taxonomy-based classification for the first provider, (b) the second predicted taxonomy-based classification for the second provider with the second assigned taxonomy-based classification for the second provider, (c) the third predicted taxonomy-based classification for the third provider with the third assigned taxonomy-based classification for the third provider; responsive to the respective comparisons, programmatically assign (a) an unknown condition to the first claim, (b) a match condition to the second claim, and (c) a not matched condition to the third claim; and responsive to assigning the unknown condition to the first claim, programmatically update the data field of the first record with the first assigned taxonomy-based classification to the first predicted taxonomy-based classification.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 2A is a schematic of an analytic computing entity in accordance with certain embodiments of the present invention;

FIG. 2B is a schematic representation of a memory media storing a plurality of repositories, databases, data stores, and/or relational tables;

Figure 5:
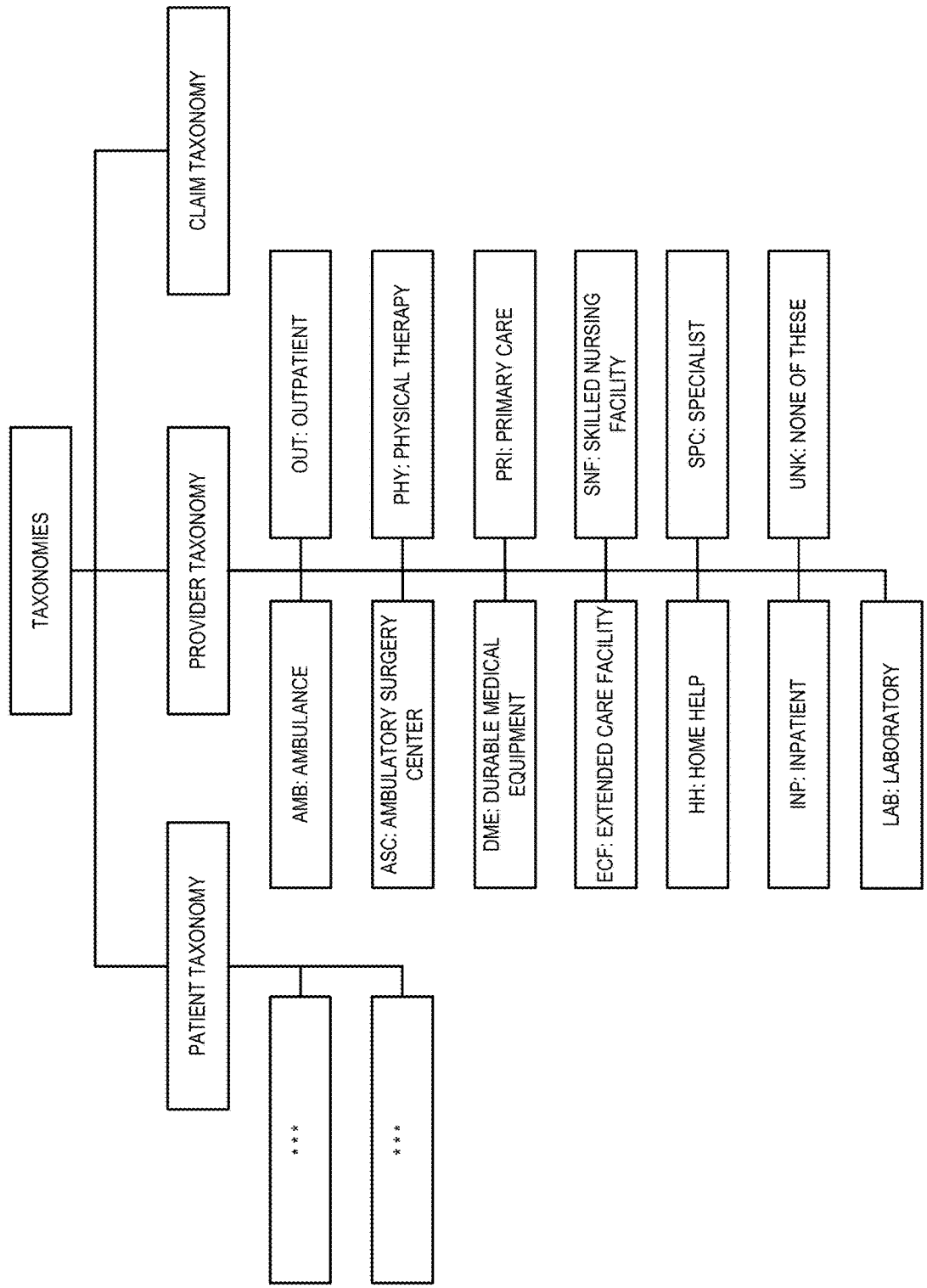
Figure 7:
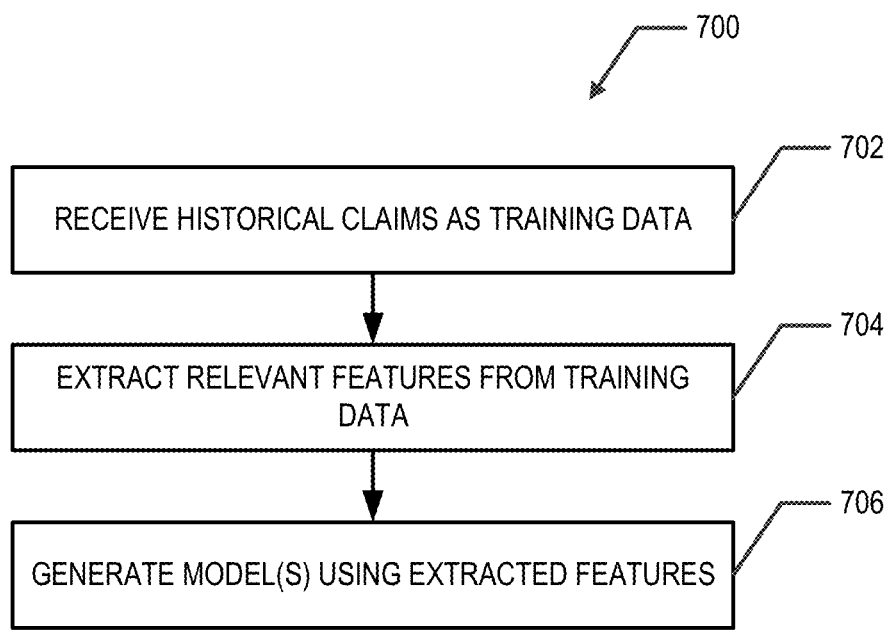
Figure 8A:
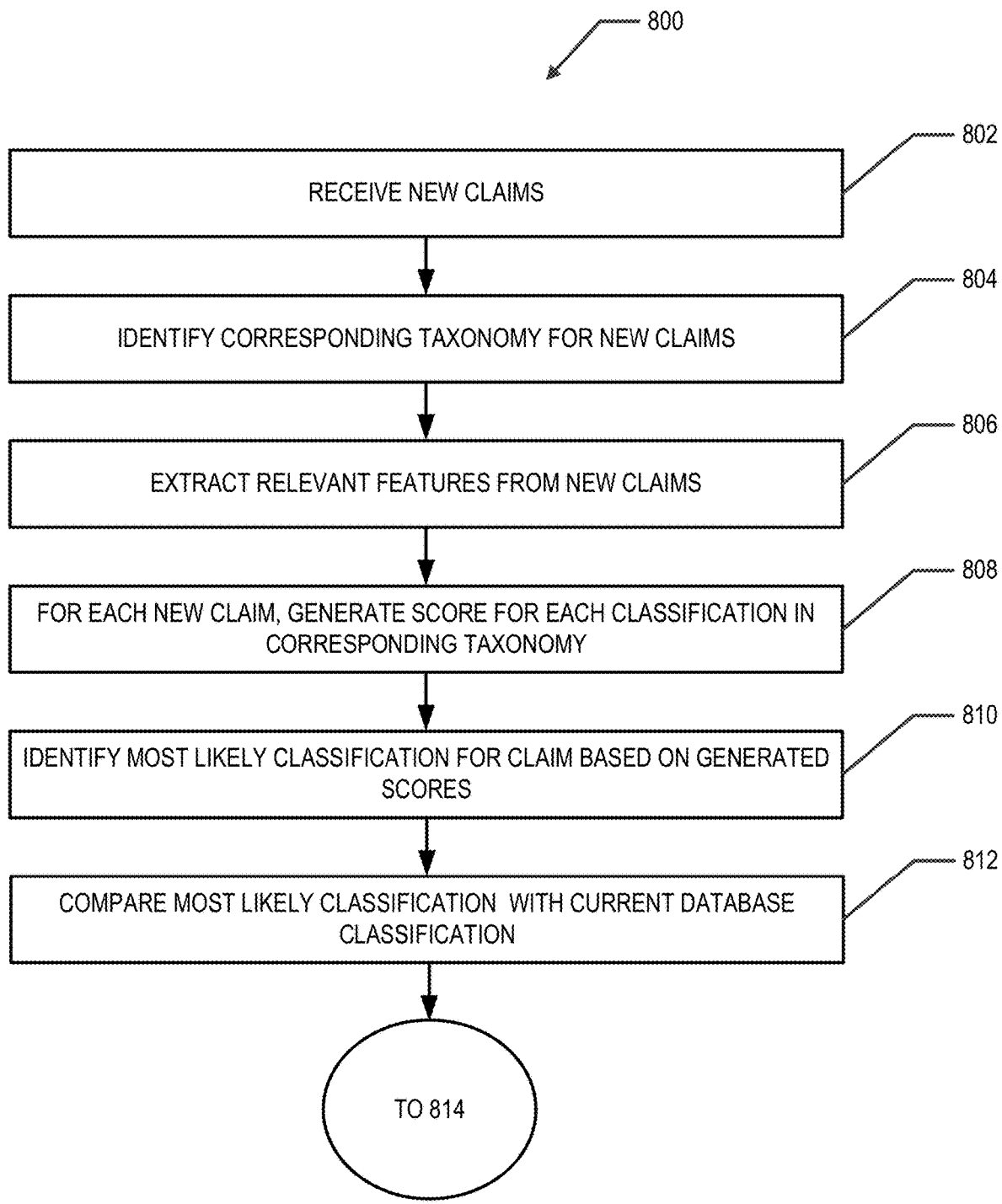
Figure 8B:
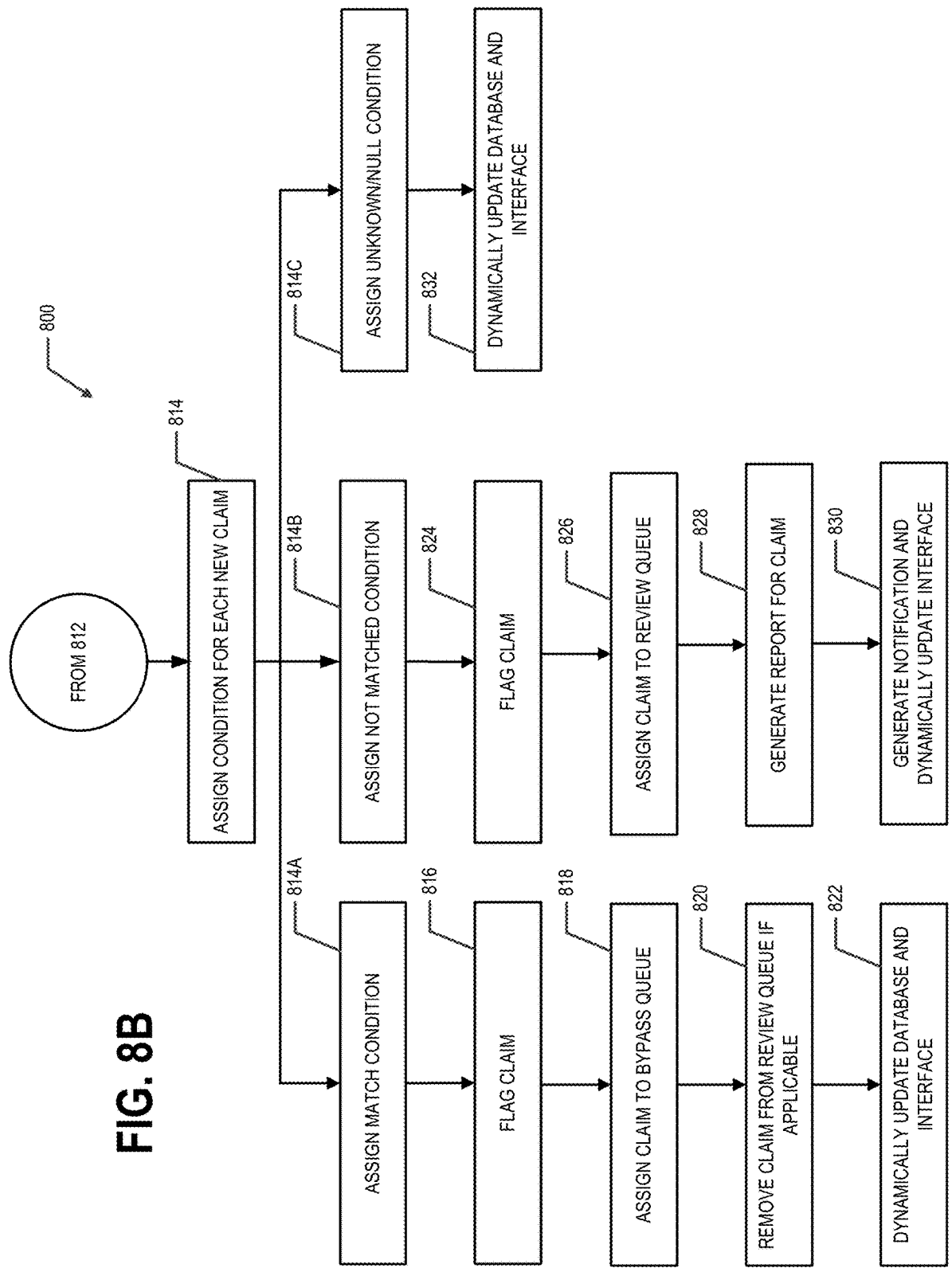
Figure 9:
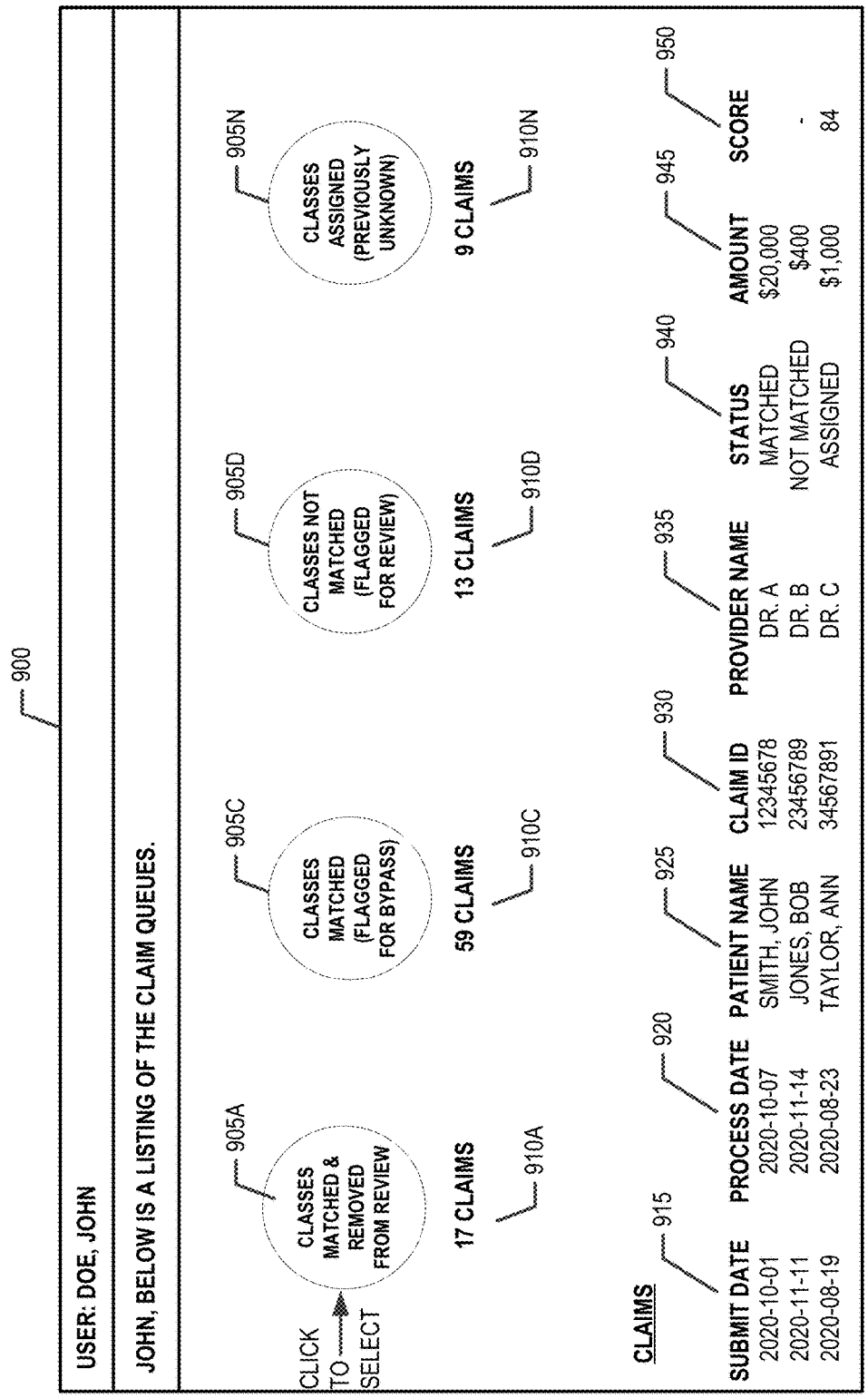

FIGS. 4A, 4B, 4C, 4D, 4E, 4F, 4G, 4H, 4I, and 4J are exemplary claims records and provider records in accordance with certain embodiments of the present invention;

FIG. 5 shows exemplary taxonomies in accordance with certain embodiments of the present invention;

FIG. 6 provides a confusion matrix for predictions on an exemplary validation dataset in accordance with certain embodiments of the present invention;

FIGS. 7, 8A, and 8B are flowcharts for exemplary operations, steps, and processes in accordance with certain embodiments of the present invention; and FIG. 9 provides an interactive user interface that is dynamically updated based at least in part on probabilistic database updates in accordance with embodiments of the present invention.

DETAILED DESCRIPTION OF SOME EXAMPLE EMBODIMENTS

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" (also designated as "/") is used herein in both the alternative and conjunctive sense, unless otherwise indicated. The terms "illustrative" and "exemplary" are used to be examples with no indication of quality level. Like numbers refer to like elements throughout.

I. COMPUTER PROGRAM PRODUCTS, METHODS, AND COMPUTING ENTITIES

Embodiments of the present invention may be implemented in various ways, including as computer program products that comprise articles of manufacture. Such computer program products may include one or more software components including, for example, software objects, methods, data structures, and/or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of a data structure, apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

II. EXEMPLARY PLATFORM ARCHITECTURE

Figure 1:
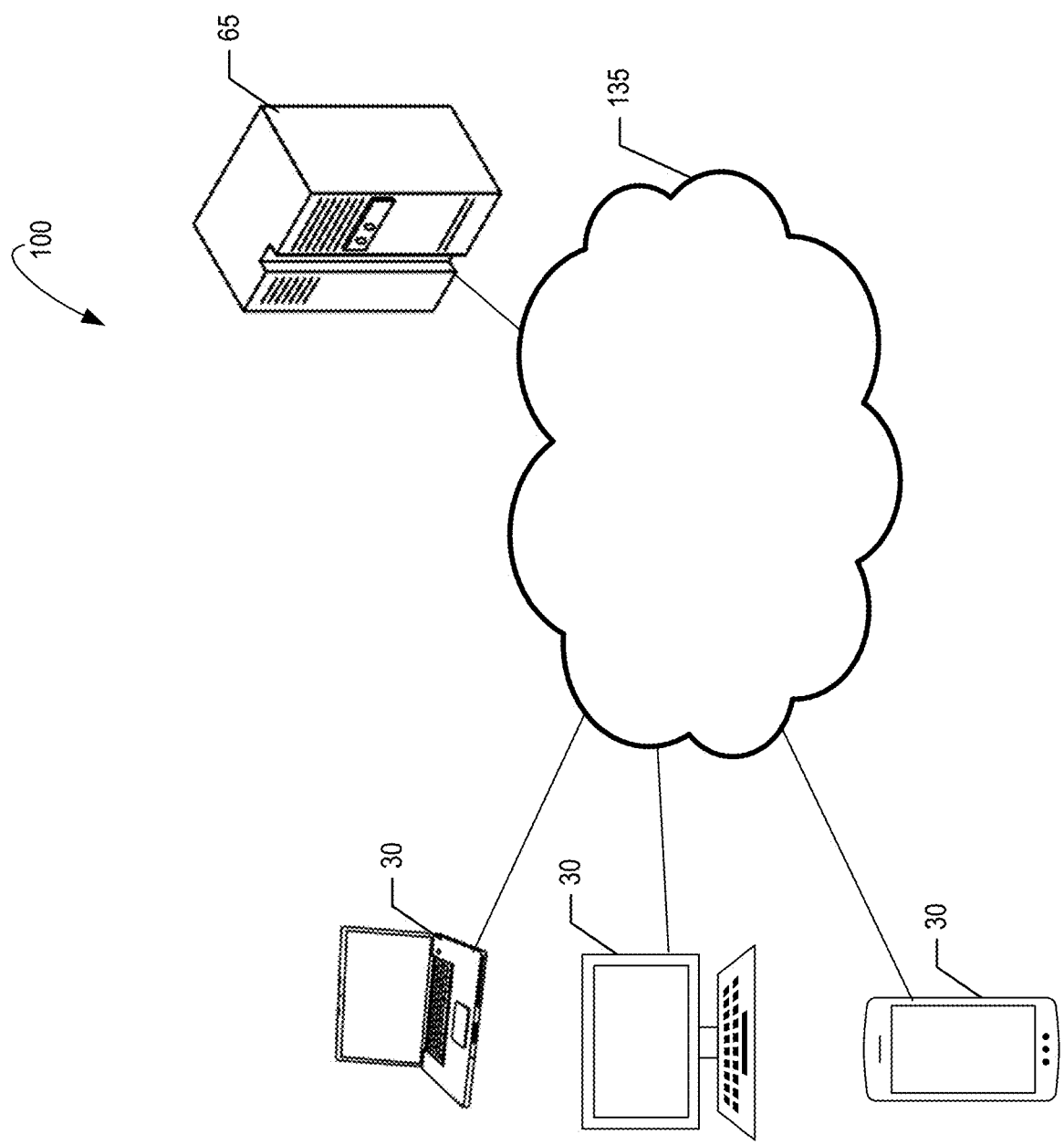
FIG. 1 is a diagram of a prediction platform that can be used in conjunction with various embodiments of the present invention.

FIG. 1 provides an illustration of a prediction platform 100 that can be used in conjunction with various embodiments of the present invention. As shown in FIG. 1, the prediction platform 100 may comprise one or more analytic computing entities 65, one or more user computing entities 30, one or more networks 135, and/or the like. Each of the components of the platform may be in electronic communication with, for example, one another over the same or different wireless or wired networks 135 including, for example, a wired or wireless Personal Area Network (PAN), Local Area Network (LAN), Metropolitan Area Network (MAN), Wide Area Network (WAN), and/or the like. Additionally, while FIG. 1 illustrate certain platform entities as separate, standalone entities, the various embodiments are not limited to this particular architecture.

Exemplary Analytic Computing Entity

FIG. 2A provides a schematic of an analytic computing entity 65 according to one embodiment of the present invention. In general, the terms computing entity, entity, device, system, and/or similar words used herein interchangeably may refer to, for example, one or more computers, computing entities, desktop computers, mobile phones, tablets, phablets, notebooks, laptops, distributed systems, items/devices, terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably. The analytic computing entity 65 may be a standalone entity or embedded as part of another platform, system, or entity.

As indicated, in one embodiment, the analytic computing entity 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the analytic computing entity 65 may communicate with other computing entities 65, one or more user computing entities 30, and/or the like.

As shown in FIG. 2A, in one embodiment, the analytic computing entity 65 may include or be in communication with one or more processing elements 205 (also referred to as processors, processing circuitry, and/or similar terms used herein interchangeably) that communicate with other elements within the analytic computing entity 65 via a bus, for example, or network connection. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the analytic computing entity 65 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 206 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media may store databases, database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably and in a general sense to refer to a structured or unstructured collection of information/data that is stored in a computer-readable storage medium.

Memory media 206 may also be embodied as a data storage device or devices, as a separate database server or servers, or as a combination of data storage devices and separate database servers. Further, in some embodiments, memory media 206 may be embodied as a distributed repository such that some of the stored information/data is stored centrally in a location within the system and other information/data is stored in one or more remote locations. Alternatively, in some embodiments, the distributed repository may be distributed over a plurality of remote storage locations only. An example of the embodiments contemplated herein would include a cloud data storage system maintained by a third party provider and where some or all of the information/data required for the operation of the prediction platform may be stored. As a person of ordinary skill in the art would recognize, the information/data required for the operation of the prediction platform may also be partially stored in the cloud data storage system and partially stored in a locally maintained data storage system.

Memory media 206 may include information/data accessed and stored by the prediction platform to facilitate the operations of the system. More specifically, memory media 206 may encompass one or more data stores configured to store information/data usable in certain embodiments. For example, as shown in FIG. 2B, data stores encompassed within the memory media 206 may comprise provider information/data 211, patient information/data 212, claim information/data 213, interaction information/data 214, and/or the like.

As illustrated in FIG. 2B, the data stores 206 may comprise provider information/data 211 with identifying/determining information/data indicative of various providers. The term provider is used generally to refer to any person or entity that provides goods, services, and/or the like. For example, the provider information/data 211 may comprise provider records/profiles, identifiers, provider locations, provider classifications (e.g., assigned taxonomy-based classifications and/or predicted taxonomy-based classifications), and/or the like.

Continuing with FIG. 2B, the data stores 206 may comprise patient information/data 212. The patient information/data 212 may comprise information/data for a patient, such as patient records/profiles, age, gender, poverty rates, known health conditions, home location, profession, access to medical care, medical history, claim history, patient identifier (ID), patient classifications (e.g., assigned taxonomy-based classifications and/or predicted taxonomy-based classifications), and/or the like.

Continuing with FIG. 2B, claim information/data may comprise claim information/data 213 indicative of claims filed on behalf of a provider for services or products. Examples of providers include medical doctors, nurse practitioners, physician assistants, nurses, other medical professionals practicing in one or more of a plurality of medical specialties (e.g., psychiatry, pain management, anesthesiology, general surgery, emergency medicine, and/or the like), hospitals, urgent care centers, diagnostic laboratories, surgery centers, and/or the like. Moreover, the claim information/data 213 may further comprise prescription claim information/data. Prescription claim information/data may be used to extract information/data such as the identity of entities that prescribe certain drugs and the pharmacies who fulfill such prescriptions. The claim information/data 213 may also queue assignment information/data indicative regarding the queue to which the claim is assigned.

The data stores 206 may further store interaction information/data 214 used by the prediction platform. For example, the interaction information/data 212 stored by the data store may comprise the type of communication, the claim to which it relates, the date of the interaction, the time of the interaction, the user (e.g., provider, patient, insurance company) associated with the interaction, and/or the like.

In one embodiment, the analytic computing entity 65 may further include or be in communication with volatile media (also referred to as volatile storage, memory, memory storage, memory circuitry and/or similar terms used herein interchangeably). In one embodiment, the volatile storage or memory may also include one or more volatile storage or memory media 207 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory media may be used to store at least portions of the databases, database instances, database management system entities, data, applications, programs, program modules, scripts, source code, object code, byte code, compiled code, interpreted code, machine code, executable instructions, and/or the like being executed by, for example, the processing element 308. Thus, the databases, database instances, database management system entities, data, applications, programs, program modules, scripts, source code, object code, byte code, compiled code, interpreted code, machine code, executable instructions, and/or the like may be used to control certain aspects of the operation of the analytic computing entity 65 with the assistance of the processing element 205 and operating system.

As indicated, in one embodiment, the analytic computing entity 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the analytic computing entity 65 may communicate with computing entities or communication interfaces of other computing entities 65, user computing entities 30, and/or the like.

As indicated, in one embodiment, the analytic computing entity 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the analytic computing entity 65 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol. The analytic computing entity 65 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

As will be appreciated, one or more of the analytic computing entity's components may be located remotely from other analytic computing entity 65 components, such as in a distributed system. Furthermore, one or more of the components may be aggregated and additional components performing functions described herein may be included in the analytic computing entity 65. Thus, the analytic computing entity 65 can be adapted to accommodate a variety of needs and circumstances.

Exemplary User Computing Entity

Figure 3:
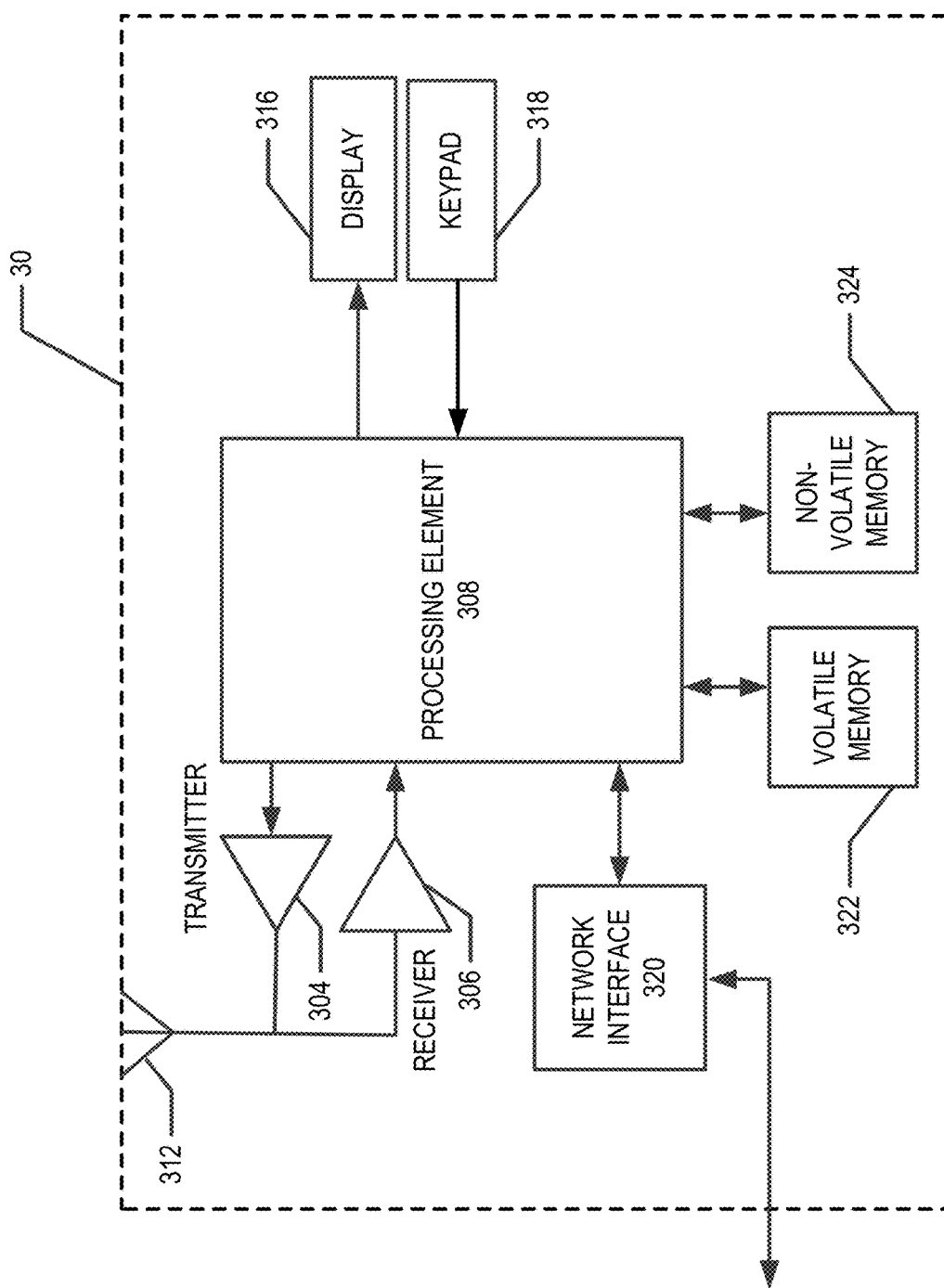
FIG. 3 is a schematic of a user computing entity in accordance with certain embodiments of the present invention.

FIG. 3 provides an illustrative schematic representative of user computing entity 30 that can be used in conjunction with embodiments of the present invention. As will be recognized, the user computing entity may be operated by an agent and include components and features similar to those described in conjunction with the analytic computing entity 65. Further, as shown in FIG. 3, the user computing entity may include additional components and features. For example, the user computing entity 30 can include an antenna 312, a transmitter 304 (e.g., radio), a receiver 306 (e.g., radio), and a processing element 308 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various entities, such as an analytic computing entity 65, another user computing entity 30, and/or the like. In this regard, the user computing entity 30 may be capable of operating with one or more air interface standards, communication protocols, modulation types, and access types. More particularly, the user computing entity 30 may operate in accordance with any of a number of wireless communication standards and protocols. In a particular embodiment, the user computing entity 30 may operate in accordance with multiple wireless communication standards and protocols, such as GPRS, UMTS, CDMA2000, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 30 can communicate with various other entities using concepts such as Unstructured Supplementary Service data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 30 can also download changes, add-ons, and updates, for instance, to its firmware, software (e.g., including executable instructions, applications, program modules), and operating system.

According to one embodiment, the user computing entity 30 may include location determining aspects, devices, modules, functionalities, and/or similar words used herein interchangeably. For example, the user computing entity 30 may include outdoor positioning aspects, such as a location module adapted to acquire, for example, latitude, longitude, altitude, geocode, course, direction, heading, speed, UTC, date, and/or various other information/data. In one embodiment, the location module can acquire data, sometimes known as ephemeris data, by identifying/determining the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data/data may be determined by triangulating the position in connection with a variety of other systems, including cellular towers, Wi-Fi access points, and/or the like. Similarly, the user computing entity 30 may include indoor positioning aspects, such as a location module adapted to acquire, for example, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing devices (e.g., smartphones, laptops) and/or the like. For instance, such technologies may include iBeacons, Gimbal proximity beacons, BLE transmitters, Near Field Communication (NFC) transmitters, and/or the like. These indoor positioning aspects can be used in a variety of settings to determine the location of someone or something to within inches or centimeters.

The user computing entity 30 may also comprise a user interface comprising one or more user input/output interfaces (e.g., a display 316 and/or speaker/speaker driver coupled to a processing element 308 and a touch screen, keyboard, mouse, and/or microphone coupled to a processing element 308). For example, the user output interface may be configured to provide an application, browser, user interface, dashboard, webpage, and/or similar words used herein interchangeably executing on and/or accessible via the user computing entity 30 to cause display or audible presentation of information/data and for user interaction therewith via one or more user input interfaces. The user output interface may be updated dynamically from communication with the analytic computing entity 65. The user input interface can comprise any of a number of devices allowing the user computing entity 30 to receive data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the user computing entity 30 and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the user computing entity 30 can collect information/data, user interaction/input, and/or the like.

The user computing entity 30 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions of the user computing entity 30.

Exemplary Networks

In one embodiment, the networks 135 may include, but are not limited to, any one or a combination of different types of suitable communications networks such as, for example, cable networks, public networks (e.g., the Internet), private networks (e.g., frame-relay networks), wireless networks, cellular networks, telephone networks (e.g., a public switched telephone network), or any other suitable private and/or public networks. Further, the networks 135 may have any suitable communication range associated therewith and may include, for example, global networks (e.g., the Internet), MANs, WANs, LANs, or PANs. In addition, the networks 135 may include any type of medium over which network traffic may be carried including, but not limited to, coaxial cable, twisted-pair wire, optical fiber, a hybrid fiber coaxial (HFC) medium, microwave terrestrial transceivers, radio frequency communication mediums, satellite communication mediums, or any combination thereof, as well as a variety of network devices and computing platforms provided by network providers or other entities.

III. EXEMPLARY SYSTEM OPERATION

Reference will now be made to FIGS. 4A, 4B, 4C, 4D, 4E, 4F, 4G, 4H, 4I, 4J, 5, 6, 7, 8A, 8B, and 9. FIGS. 4A, 4B, 4C, 4D, 4E, 4F, 4G, 4H, 4I, and 4J show exemplary claims records. FIG. 5 shows exemplary taxonomies. FIG. 6 provides a confusion matrix for predictions on an exemplary validation dataset. FIGS. 7, 8A, and 8B are flowcharts for exemplary operations, steps, and processes. And FIG. 9 provides an interactive user interface that is dynamically updated based at least in part on probabilistic database updates.

Technical Solutions

As indicated, there is a latent need for a rigorous methodology that can automatically predict prediction an appropriate classification for a claim by assigning a probability of belonging to a classification in a taxonomy from the claim level claim to the claim service line level (the most granular level available). Embodiments of the present invention only need rely on information/data submitted on the reimbursement claim form for classification (without human aid or intervention). Embodiments of the present invention are also used to create a database of taxonomies that can validate a self-reported taxonomy and also automatically assign a classification and update a database when that a classification is missing. Embodiments are also useful in fraud detection and navigating interactive interfaces. Such operations are incapable of human performance.

Records/Profiles

In one embodiment, a user (e.g., provider, patient, insurance company employee or representative, and/or the like) may interact with and navigate a user interface, such as user interface 900, through operation of a user computing entity 30. Through the user interface 900, for example, the user (e.g., provider, patient, insurance company employee or representative, and/or the like) may view and access claim information/data, patient information/data, provider information/data, and/or the like. To do so, the prediction platform 100 may provide access to the system via a user record/profile that has been previously established and/or stored. In an example embodiment, a user record/profile comprises user record/profile information/data, such as a user identifier configured to uniquely identify/determine the user (e.g., provider identifier, patient identifier, and/or the like), a username, user contact information/data (e.g., name, one or more electronic addresses such as emails, instant message usernames, social media user name, and/or the like), user preferences, user account information/data, user credentials, information/data identifying/determining one or more user computing entities 30 corresponding to the user, and/or the like. Moreover, each user and/or user record/profile may correspond to a unique username, unique user identifier (e.g., 11111111), access credentials, and/or the like. With the user record/profile providing access to information/data through the user interface 900, the user can access and navigate the same. As will be recognized, a user may be a patient, patient representative, provider, provider representative, healthcare insurance representative or employee, and/or the like.

In one embodiment, a patient record/profile (stored by and/or accessible via one more databases) may comprise a subset of patient information/data or patient features that can be associated with a given patient, claim, and/or the like. As used herein, the term patient may refer to a person who receives healthcare services or products rendered by a provider and/or who relies on financing from a health insurance payer to cover the costs of the rendered health services or products. In that sense, a patient may be associated with the health insurance payer and may be considered a patient (or member) of (a program associated with) the health insurance payer. In one embodiment, patient features can include, but are not limited to, age, gender, poverty rates, known health conditions, home location, profession, access to medical care, medical history, claim history, patient identifier, assigned taxonomy-based classifications, predicted taxonomy-based classifications, and/or the like.

In one embodiment, a provider record/profile (stored by and/or accessible via one more databases) may comprise a subset of provider information/data or provider features that can be associated with a given provider, claim, and/or the like. FIGS. 4B, 4E, 4H, and 4J are provider records/profiles (or portions of information/data contained therein). As indicated, a provider may refer to a person or entity that provides services or products. In at least one embodiment, in the health care context, providers rely on a health insurance payers to finance or reimburse the cost of the services or products provided to patients. For example, a provider may comprise a health professional operating within one or more of a plurality of branches of healthcare, including medicine, surgery, dentistry, midwifery, pharmacy, psychology, psychiatry, pain management, nursing, laboratory diagnostics, and/or the like. Further, a provider may also comprise an organization, such as a private company, hospital, laboratory, or the like, that operates within one or more of a plurality of branches of healthcare. Each provider may be associated with provider features that include, but are not limited to, demographics (e.g., the location in which the provider operations), contracted status, specialty, one or more taxonomy-based classifications, and/or one or more taxonomy-based classification predictions/scores. That is, each provider may be assigned or associated with one or more predicted taxonomy-based classifications and one or more taxonomy-based classification predictions/scores. For example, FIG. 5 provides an exemplary listing of multiple taxonomies, including a provider taxonomy. In this example, the provider taxonomy comprises 13 distinct classifications/classes to which or with which a provider may be assigned or associated.

Claim Information/Data

Embodiments of the present invention can be used with a variety of claims. In a particular embodiment, the claims may be healthcare claims. A healthcare claim represents a request for payment/reimbursement for services rendered, materials used, equipment provided, and/or the like. For example, a claim may be a request for payment/reimbursement for a consultation with a primary care doctor, a medical procedure or an evaluation performed by an orthopedic surgeon, a laboratory test performed by a laboratory, a surgery, durable medical equipment provided to an injured patient, medications or other materials used in the treatment of a patient, and/or the like. As will be recognized, though, embodiments of the present invention are not limited to the medical context. Rather, they may be applied to a variety of other settings.

In one embodiment, each claim may be stored as a record that comprises a description of the type of claim to which the record corresponds and comprises patient features, claim features, provider features, interaction features, and/or the like. The various features and feature sets can be extracted in a manual, semi-automatic, and/or automatic manner for a given claim.

FIGS. 4A, 4D, and 4G provides exemplary claim information/data or claim features associated with a given claim, patient, provider, and/or communication as it is submitted for payment. The terms information, data, features, and other terms are used herein interchangeably. The claim features may continuously change (e.g., be time-dependent) for many reasons, such as the prevalence of certain diseases, the emergence of new diseases (e.g., representing new claim), and/or previous medical codes being introduced and/or discontinued.

Example claim features may include a claim ID and the date and time the claim was received. The claim features may also include one or more diagnostic codes, treatment codes, treatment modifier codes, and/or the like. Such codes may be any code, such as Current Procedural Terminology (CPT) codes, billing codes, Healthcare Common Procedure Coding System (HCPCS) codes, ICD-10-CM Medical Diagnosis Codes, and/or the like.

As an example of billing codes, a patient may visit a doctor because of discomfort in his lower leg. During the visit, the doctor may examine the patient's lower leg and take an x-ray of the lower leg as part of an examination. The claim for the visit may have multiple distinct billing codes, such as billing code 99213 and billing code 73590. Billing code 99213 may be used to request payment/reimbursement for the visit, examination, and evaluation of the patient. Billing code 73590 may be used to request payment/reimbursement for the x-ray of the leg. Using such codes and code sets, various correlations can be determined as they related to recoverability. Each claim may have a state and status. The states may be original, pre-adjudicated, or post-adjudicated. The three states relate to where the claim is in the process of being reviewed with a corresponding determination being made as to the claim's status. In addition to a state, a claim may also have a status: paid, denied, in process, appealed, appeal denied, overpaid, and/or the like. And further, each claim may be assigned to one or more electronic queues, such as a standard queue, bypass queue, and/or review queue.

From a process standpoint, once a claim is submitted, either through an online portal, through mail, through one or more APIs, and/or the like, the health insurance company starts its programmatic review of the claim. Once the review is complete (which may also include a manual review), the claim is either rejected, modified, or paid in full.

Claim information/data may include a subset of patient information/data or patient features that can be associated with a given patient, claim, and/or the like. As noted above, the term patient may refer to a person who receives healthcare services or products rendered by a provider and/or who relies on financing from a health insurance payer to cover the costs of the rendered health services or products. In that sense, a patient is associated with the health insurance payer and is said to be a patient of (a program associated with) the health insurance payer. In one embodiment, patient features can include, but are not limited to, age, gender, poverty rates, known health conditions, home location, profession, access to medical care, assigned or predicted patient classifications, medical history, claim history, patient identifier, and/or the like.

Claim information/data may further include a subset of provider information/data or provider features that can be associated with a given provider, claim, and/or the like. As noted above, a provider may refer to a person or entity that provides services or products. In at least one embodiment, in the health care context, providers rely on a health insurance payers to finance or reimburse the cost of the services or products provided. For example, a provider may comprise a health professional operating within one or more of a plurality of branches of healthcare, including medicine, surgery, dentistry, midwifery, pharmacy, psychology, psychiatry, pain management, nursing, laboratory diagnostics, and/or the like. A provider may also comprise an organization, such as a private company, hospital, laboratory, or the like, that operates within one or more of a plurality of branches of healthcare. Each provider may be associated with provider features that include, but are not limited to, demographics (e.g., the location in which the provider operations), contracted status, specialty, one or more assigned or predicted provider classifications, one or more predicted provider classification scores for the provider. The predicted provider classification score may indicate the level of confidence for the predicted provider classification. Similar to claim features, provider features can continuously change (e.g., be time-dependent) for several reasons. For instance, within a given provider, the software, policies for submitting claims, personnel, strategies for submitting claims, experience, and/or the like may change in an unpredictable manner and result in a sudden change to the recoverability associated with that provider.

Generating and Training Machine Learning Model(s)

As indicated at steps/operations 702, 704, and 706 of process 700, the analytic computing entity 65 can obtain, access, receive, and/or similar words used herein interchangeably historical claims comprising historical claim information/data. The number of claims may range and include hundreds of thousands to millions of individual claim lines. With the historical claims, the analytic computing entity 65 can extract the relevant features to generate and train one or more machine learning models to predict taxonomy-based classifications for claims. That is, the target variable is a classification in a taxonomy, such as a provider classification. FIG. 5 provides three taxonomies: a patient taxonomy, a claim taxonomy, and a provider taxonomy. In the provider the taxonomy, there are thirteen provider classifications: AMB (Ambulance), ASC (Ambulatory Surgery Center), DME (Durable Medical Equipment), ECF (Extended Care Facility), HH (Home Help), INP (Inpatient), LAB (Laboratory), OUT (Outpatient), PHY (Physical Therapy), PRI (Primary Care), SNF (Skilled Nursing Facility), SPC (Specialist), and UNK (Unknown or None). Thus, in this example, the one or more machine learning models are configured to generate predicted provider classifications (e.g., predict provider classifications).

As will be recognized, the training features may vary. In one embodiment, exemplary features for training the one or more machine learning models may include bill type codes; DRG codes, diagnosis codes, procedure codes, derived features; provider PAR/NPAR statuses; patient discharge status codes; allowed amounts; charged amounts, whether the claim was allowed/denied, and/or the like. As noted, a variety of other features of interest may be used to generate and train the models.

In one embodiment, a variety of machine learning libraries and algorithms can be used to implement embodiments of the present invention. For example, gradient boosting, gradient boosting with H2O, random forest, neural networks, decision trees, and/or various other machine learning techniques can be used to adapt to different needs and circumstances. In one embodiment, the one or more machine learning models may be pluggable machine learning models. A pluggable machine learning model can be download and installed to make machine learning easier to use, extensible, and interchangeable and or embedded as part of another system or entity. The one or more machine learning models can be generated and trained using the extracted features from the historical claims.

After generation and initial training, the one or more models can be validated using an unseen/new validation dataset. The validation dataset allows for further refinement of the models. FIG. 6 provides a confusion matrix for predictions on an exemplary validation dataset. In FIG. 6, the row names are the recorded classifications, and the column names show the model predictions. Using a particular model that can be further refined, the following are exemplary observations of FIG. 6:

Depending on the model, certain classifications are very well predicted. For example, using a particular model, the following categories are well predicted: AMB, DME, ECF, INP, SNF, PHY.

After generation and initial training, there may be some confusion prior to refinement:

Before retraining (e.g., refinement and/or optimization) of the model, OUT may be confused with both PRI and SPC;

Before retraining (e.g., refinement and/or optimization) of the model, UNK may be predicted across multiple categories, but mostly PRI or SPC;

Before retraining (e.g., refinement and/or optimization) of the model, ASC may be confused with INP;

Before retraining (e.g., refinement and/or optimization) of the model, HH may be confused with DME, PRI, SNF, or SPC;

Before retraining (e.g., refinement and/or optimization) of the model, LAB may be confused with PRI or SPC; and Before retraining (e.g., refinement and/or optimization) of the model, OUT may be confused with PRI or SPC.

Thus, after generation and initial training and based at least in part on the validation dataset, the one or more machine learning models can be retrained (e.g., refined and/or optimized). In one embodiment, the prediction platform 100 (e.g., via an analytic computing entity 65) can retrain the one or more machine learning models on a regular or continuous basis or in response to certain triggers. This may be necessary because claim features and influencing factors can vary over time. In one embodiment, the prediction platform 100 (e.g., via an analytic computing entity 65) may retrain when actions occur for a claims (e.g., being denied, paid, accessed, appealed, and/or the like) on a regular basis. As will be recognized, a variety of other approaches and techniques can be used to adapt to various needs and circumstances.

As a result of the generating, training, and/or retraining, the one or more machine learning models are configured to subsequently predict taxonomy-based classification scores of unseen/new claims. As will be appreciated, the hidden and/or weak correlations found as a result of the one or more machine learning models are simply not practical for human-implementation.

Generating Predicted Taxonomy-Based Classifications

As indicated by process 800 of FIGS. 8A and 8B, with one or more machine learning models trained, the prediction platform 100 (e.g., via an analytic computing entity 65) can use the one or more machine learning models to generate predicted taxonomy-based classification scores for any unseen/new claims. This can be performed in batch or in real-time. As part of that process, as indicated by steps/operations 802, 804, and 806, when a claim is received, the prediction platform 100 (e.g., via an analytic computing entity 65) can identify/determine the relevant taxonomy for the claim. For example, in one embodiment, there may be a plurality of taxonomies that may apply to a given claim, such as a provider taxonomy, a patient taxonomy, or a claim taxonomy. Each taxonomy may identify/determine one or more features that are to be extracted from a given claim to generate a prediction. Thus, the prediction platform 100 (e.g., via an analytic computing entity 65) can extract the relevant features of the claim (with or without the aid of the corresponding taxonomy) for input into the one or more machine learning models. This may include retrieving additional information/data about patients, providers, interactions, and/or the like associated with the claim. This may also include formatting the features (e.g., into a feature vector) for input into the one or more machine learning models.

The features can then be input into the one or more machine learning models to generate a taxonomy-based classification score for each classification in the corresponding taxonomy (e.g., step/operation 808 of FIG. 8A). Continuing with the above example, for each claim, the one or more machine learning models (e.g., via an analytic computing entity 65) outputs thirteen taxonomy-based provider classification scores—one for each classification in the taxonomy. Below is an exemplary output of thirteen scores for claim 12345678 of FIG. 4A: AMB: 0.43, ASC: 0.38, DME: 0.97, ECF: 0.05, HH: 0.54, INP: 0.63, LAB: 0.57, OUT: 0.29, PHY: 0.07, PRI: 0.86, SNF: 0.01, SPC: 0.65, and UNK: 0.44. As will be recognized, this may be performed for multiple claims using real-time or batch processing and processing the claims in a parallel serial manner. For example, claims can be scored in real-time as they are received (individually or in batch). Thus, responsive to the prediction platform 100 (e.g., via an analytic computing entity 65) receiving one or more unseen/new claims, the prediction platform 100 (e.g., via an analytic computing entity 65) can score (e.g., generate a predicted taxonomy-based classification score for) the one or more unseen/new claims. The predicted taxonomy-based classification score may be in a variety of domains, such as [0,1]. In this example, the higher the output, the higher the likelihood that predicted classification is correct for the corresponding claim. Similarly, the lower the output number, the lower the likelihood that predicted classification is correct for the corresponding claim. The predicted taxonomy-based classification scores can be stored in a permanent or temporary data structure intended for the same. The data structure may be identifiable by the claim identifier, one or more provider identifiers, and/or one or more patient identifiers. The data structure can be linked or connected to the claim, patient, or provider. As will be recognized, because claim features are highly dynamic and change continuously during a given time period, claim scoring can occur in a similar manner.

At step/operation 810, the prediction platform 100 (e.g., via an analytic computing entity 65) can identify/determine the most likely classification for the claim based at least in part on the taxonomy-based classification scores. Continuing with the above example, the following includes the scores sorted in ascending order for claim 12345678—SNF: 0.01, OUT: 0.29, ASC: 0.38, AMB: 0.43, UNK: 0.44, ECF: 0.05, HH: 0.54, LAB: 0.57, INP: 0.63, SPC: 0.65, PHY: 0.07, PRI: 0.86, and DME: 0.97. Thus, the prediction platform 100 (e.g., via an analytic computing entity 65) identifies DME (with a score of 0.97) as being the most likely or accurate prediction based at least in part on it being closest to the upper end of the domain for claim 12345678. Similar predictions and identifications are performed for claim 23456789 of FIG. 4D and claim 34567891 of FIG. 4G. For claim 23456789 of FIG. 4D, the prediction platform 100 (e.g., via an analytic computing entity 65) identifies AMB (with a score of 0.63) as being the most likely or accurate prediction based at least in part on it being closest to the upper end of the domain. For claim 34567891 of FIG. 4G, the prediction platform 100 (e.g., via an analytic computing entity 65) identifies PRI (with a score of 0.84) as being the most likely or accurate prediction based at least in part on it being closest to the upper end of the domain.

At step/operation 812, the prediction platform 100 (e.g., via an analytic computing entity 65) retrieves, obtains, receives, or access a classification from the appropriate data field from the database storing a corresponding record/profile for comparison. In certain embodiments, the classification information/data received before during, after, or as part of the above processing (e.g., it may be received with the claim). After retrieving the corresponding classification, the prediction platform 100 (e.g., via an analytic computing entity 65) compares the retrieved classification with the most likely or accurate predicted classification and assigns a corresponding condition. Moreover, the prediction platform 100 (e.g., via an analytic computing entity 65) will store or have access to the taxonomy along with a corresponding date of record, such as in a database structure. Additional columns will record the newly identified taxonomy, along with the date of record for the new taxonomy, and any results from validation of the imputed taxonomy resulting from manual investigation. This database will be dynamic and be continually updated by as new claims are scored.

Matching Condition for Claim

For claim 12345678 of FIG. 4A, the prediction platform 100 (e.g., via an analytic computing entity 65) retrieves the listed provider classification for Dr. A using AAAAAAAA (the Provider ID) as the key. Thus, for claim 12345678, the prediction platform 100 (e.g., via an analytic computing entity 65) retrieves DME from the appropriate data field from Dr. A's record/profile from the database for comparison with the predicted classification (see FIG. 4B). Then, the prediction platform 100 (e.g., via an analytic computing entity 65) compares programmatically DME (predicted taxonomy-based classification) to DME (the assigned taxonomy-based classification) and determines that the values match (steps/operations 814 and 814A) and assigns match condition to claim 12345678.

Because the provider classifications match, the likelihood of provider fraud (based at least in part on the provider classification) is reduced. With the reduced likelihood of fraud, the prediction platform 100 (e.g., via an analytic computing entity 65) assigns claim 12345678 to an electronic bypass queue 905B (step/operation 816). As will be recognized, a queue is a sequence of work objects that are waiting to be processed. A queue may be implemented using transient data structures, non-transient data structures, tags, queue assignment rules, queue priority rules, queue workload balancing rules, and/or the like. And a bypass is a queue comprising claims that are less likely to have provider fraud based at least in part on the provider classifications submitted with the claims. Thus, the claims in the bypass queue may not require as much scrutiny or review as other claims. It should be recognized that the claim may still be filtered from fraud and abuse analytics that target shifting billing patterns, pass-through billing, or phantom billing. Analytics from which the claim will be filtered can be identified by an edit ID. And the claim may still be stopped by other edits (based at least in part on policy, other coding practices, and/or the like).

In one embodiment, the prediction platform 100 (e.g., via an analytic computing entity 65) can also update (a) the record/profile for the provider (not shown) with the most-recent confidence score, (b) the claim to include the predicted taxonomy-based classification score for the corresponding predicted taxonomy-based classification (FIG. 4C), and (c) a dynamically updatable interface 900.

At step/operation 820, if a provider has been manually verified as having legitimate reasons (not related to fraud or abuse) for billing outside of the corresponding specialty, or if the algorithmic derived provider taxonomy matches the taxonomy of record, then the prediction platform 100 (e.g., via an analytic computing entity 65) can automatically remove any claims from claims currently assigned to a review queue for the provider and reassign them to a standard queue for normal claims processing. The prediction platform 100 (e.g., via an analytic computing entity 65) can perform this process in an automated manner and allow a previously flagged claim to continue through the standard adjudication process as if no mismatch of taxonomy had ever taken place.

Not Matching Condition for Claim

For claim 23456789 of FIG. 4D, the prediction platform 100 (e.g., via an analytic computing entity 65) retrieves the listed provider classification for Dr. B using BBBBBBBB (the Provider ID) as the key. Thus, for claim 23456789, the prediction platform 100 (e.g., via an analytic computing entity 65) retrieves SNF from the appropriate data field from Dr. B's record/profile from the database for comparison with the predicted classification (see FIG. 4E). Then, the prediction platform 100 (e.g., via an analytic computing entity 65) compares SNF to AMB and determines that the values do not match (steps/operations 814 and 814B) and assigns the corresponding condition to claim 23456789.

Because of the not matching condition, the prediction platform 100 (e.g., via an analytic computing entity 65) flags claim 23456789 for review (and potential fraud). The flag or indication is indicative that there is potential for fraud in the claims and may be a binary label or indication of "Y" or "1" for yes or an "N" or "0" (step/operation 822). The prediction platform 100 (e.g., via an analytic computing entity 65) also assigns the claim to an electronic review queue (step/operation 824). A review queue 905C is a queue comprising claims that have an indication that the claims may be fraudulent and are therefore submitted for a specialized manual, semi-automatic, or automatic review. Thus, the claims in the review queue require the increased scrutiny or review as would normally be performed.

In addition to flagging the claim for review and assigning it to an electronic review queue, the prediction platform 100 (e.g., via an analytic computing entity 65) can automatically generate a report for the claim (step/operation 826). Continuing with the above example, the prediction platform 100 (e.g., via an analytic computing entity 65) may generate a PDF report that identifies the differences in the provider classifications, the corresponding scores, the claim, and other historical information/data (e.g., associated with the provider or patient. The report can be included as part of a notification provided at step/operation 828. As will be recognized, a variety of reports and reporting formats can be used to adapt to various needs and circumstances.

Further, at step/operation 828, the prediction platform 100 (e.g., via an analytic computing entity 65) can also update the claim to include the predicted taxonomy-based classification score for the corresponding predicted taxonomy-based classification (FIG. 4C), and a dynamically updatable interface 900. As shown in FIG. 9, the review queue 905C comprises an indication (dashed highlighting) that there are claims to be reviewed in the queue. The prediction platform 100 (e.g., via an analytic computing entity 65) can also generate notifications, alerts, and/or the like that a particular claim has been flagged for potential fraud. The notifications, alerts, and/or the like may also include the report generated at step/operation 826 for the claim. As will be recognized, a variety of other approaches and techniques can be used to adapt to various needs and circumstances.

Unknown Condition for Claim

For claim 34567891 of FIG. 4G, the prediction platform 100 (e.g., via an analytic computing entity 65) retrieves the listed provider classification for Dr. C using CCCCCCCC (the Provider ID) as the key. Thus, for claim 34567891, the prediction platform 100 (e.g., via an analytic computing entity 65) does not retrieve a value (or retrieves a null, empty, unknown, and not populated value) from the appropriate data field from Dr. C's record/profile from the database for comparison with the predicted classification (see FIG. 4H). Then, the prediction platform 100 (e.g., via an analytic computing entity 65) determines that the classification for Dr. C has not been populated (steps/operations 814 and 814C) and assigns a null, empty, unknown, or not populated condition to claim 34567891.

Because of the null, empty, unknown, or not populated condition, the prediction platform 100 (e.g., via an analytic computing entity 65) assigns claim 34567891 to an electronic standard queue (step/operation 830). A standard queue 905D is a queue comprising claims that have no indication as to the likelihood of provider fraud and are therefore submitted for standard claims processing. Thus, the claims in the standard queue require the same scrutiny or review as would normally be performed.

Further, at step/operation 832, the prediction platform 100 (e.g., via an analytic computing entity 65) can also update the record/profile for the provider to include the predicted taxonomy-based classification (and/or the corresponding predicted taxonomy-based classification score). FIG. 4J shows an instance in which the prediction platform 100 (e.g., via an analytic computing entity 65) populated the data field in the record/profile for Dr. C in the database. In some embodiments, this may include inserting a field (column) in a provider row. Still further, this may include inserting a row (or similar structure) to add a new provider. the prediction platform 100 (e.g., via an analytic computing entity 65) can also update the claim to include the predicted taxonomy-based classification score for the corresponding predicted taxonomy-based classification (FIG. 4I) and/or a dynamically updatable interface 900.

Dynamic Interface

In one embodiment, users (e.g., providers, patients, insurance company employees or representatives, and/or the like) can review, access, inquire about, interact with, and/or the like with claim information/data (e.g., claim information/data). For example, a user (e.g., provider, patient, insurance company employee or representative, and/or the like) may navigate a user interface 900 by operating a user computing entity 30 to view and access claim information/data, patient information/data, provider information/data, interaction information/data, and/or the like.

As indicted, the prediction platform 100 can create and/or update claim queues, such as a removed-from-review queue 905A, a bypass queue 905B, a review queue 905C, and a standard queue 905D. As indicated above, the prediction platform 100 can provide access for viewing, investigating, and/or navigating the claims and claim queues via a user interface 900 being displayed by a user computing entity 30. Thus, the user interface 900 can be dynamically updated to show the claims associated with the corresponding queue (or the most-recent claims).

As shown via the user interface 900 of FIG. 9, the user interface may comprise various features and functionality for accessing, viewing, investigating, and/or navigating claims and claim queues. In one embodiment, the user interface 900 may identify the user (e.g., provider, patient, insurance company employee or representative, and/or the like) credentialed for currently accessing the user interface 900 (e.g., John Doe). The user interface 900 may also comprise messages to the user in the form of banners, headers, notifications, and/or the like.

As noted above, the user interface 900 may display one or more queue elements 905A-905D and/or the like for each queue. The present example provides four separate queue elements 905A-905D that, when selected, cause the corresponding claims for the queue to be displayed. The terms elements, indicators, graphics, icons, images, buttons, selectors, and/or the like are used herein interchangeably. In one embodiment, each element 905A-905D may be selected to control what the user interface 900 displays as the information/data in elements 915, 920, 925, 930, 935, 940, 945, 950, and/or the like. For example, if element 905A is selected via a user computing entity 30 (for the corresponding queue), elements 915, 920, 925, 930, 935, 940, 945, and 950 are dynamically populated with information/data corresponding to claims in the removed-from-review queue 905A.

In one embodiment, element 915 may represent the claim submission date), and element 920 may represent the claim process date. Selection of these elements may sort the claims based at least in part on the corresponding information. Elements 925 and 930 may be selectable elements for sorting and represent patient names and claim identifiers for claims that were submitted, processed, and/or flagged. Element 935 may be selectable for sorting and represent the provide name corresponding to the claim. Elements 940, 945, and 950 may be selectable for sorting and represent the status of the claim, the amount of the claim, and the taxonomy-based classification score of the claim. As will be recognized, the described elements are provided for illustrative purposes and are not to be construed as limiting the dynamically updatable interface in any way. As indicated above, the user interface 900 can be dynamically updated to adapt to a variety of needs and circumstances.

VI. CONCLUSION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method comprising:
identifying, by one or more processors, a taxonomy comprising a plurality of classifications;
storing, by the one or more processors, (a) a first record for a first provider in a datastore, wherein the first record comprises a data field with a first assigned taxonomy-based classification for the first provider from the plurality of classifications in the taxonomy, (b) a second record for a second provider in the datastore, wherein the second record comprises a data field with a second assigned taxonomy-based classification for the second provider from the plurality of classifications in the taxonomy, and (c) a third record for a third provider in the datastore, wherein the third record comprises a data field with a third assigned taxonomy-based classification for the third provider from the plurality of classifications in the taxonomy, wherein the first assigned taxonomy-based classification for the first provider is selected from a group consisting of null, empty, unknown, and not populated;
generating, by the one or more processors and one or more machine learning models, (a) for a first claim for the first provider and based at least in part on first claim data, a first plurality of predicted taxonomy-based classification scores, wherein the first plurality of predicted taxonomy-based classification scores comprises a predicted taxonomy-based classification score for each classification in the taxonomy, (b) for a second claim for the second provider and based at least in part on second claim data, a second plurality of predicted taxonomy-based classification scores, wherein the second plurality of predicted taxonomy-based classification scores comprises a predicted taxonomy-based classification score for each classification in the taxonomy, and (c) for a third claim for the third provider and based at least in part on third claim data, a third plurality of predicted taxonomy-based classification scores, wherein the third plurality of predicted taxonomy-based classification scores comprises a predicted taxonomy-based classification score for each classification in the taxonomy;

programmatically identifying, by the one or more processors, (a) a first predicted taxonomy-based classification for the first claim from the first plurality of predicted taxonomy-based classification scores, (b) a second predicted taxonomy-based classification for the second claim from the second plurality of predicted taxonomy-based classification scores, and (c) a third predicted taxonomy-based classification for the third claim from the third plurality of predicted taxonomy-based classification scores, wherein (i) the second predicted taxonomy-based classification for the second claim is equivalent to the second assigned taxonomy-based classification for the second provider, and (ii) the third predicted taxonomy-based classification for the third claim is not equivalent to the third assigned taxonomy-based classification for the third provider;

programmatically comparing, by the one or more processors, (a) the first predicted taxonomy-based classification for the first provider with the first assigned taxonomy-based classification for the first provider, (b) the second predicted taxonomy-based classification for the second provider with the second assigned taxonomy-based classification for the second provider, and (c) the third predicted taxonomy-based classification for the third provider with the third assigned taxonomy-based classification for the third provider;

responsive to the respective comparisons, programmatically assigning, by the one or more processors, (a) an unknown condition to the first claim, (b) a match condition to the second claim, and (c) a not matched condition to the third claim, wherein (i) the unknown condition is assigned to any claim whose corresponding assigned taxonomy-based classification is selected from the group consisting of null, empty, unknown, and not populated, (ii) the match condition is assigned to any claim whose corresponding assigned taxonomy-based classification and respected predicted taxonomy-based classification are equivalent, and (iii) the not matched condition is assigned to any claim whose corresponding assigned taxonomy-based classification and respective predicted taxonomy-based classification are not equivalent; and responsive to assigning the unknown condition to the first claim, programmatically updating the data field of the first record with the first assigned taxonomy-based classification to the first predicted taxonomy-based classification.

2. The computer-implemented method of claim 1 further comprising, responsive to assigning the match condition to the second claim, programmatically assigning the second claim to an electronic bypass queue.

3. The computer-implemented method of claim 2 further comprising updating a user interface to indicate assignment of the second claim to the electronic bypass queue.

4. The computer-implemented method of claim 1 further comprising, responsive to assigning the not matched condition to the third claim, programmatically assigning the third claim to an electronic review queue.

5. The computer-implemented method of claim 4 further comprising updating a user interface to indicate assignment of the third claim to the electronic review queue, wherein updating the user interface comprises generating a notification.

6. The computer-implemented method of claim 1 further comprising automatically reassigning a fourth claim assigned to an electronic review queue to a standard queue.

7. A computer program product comprising a non-transitory computer readable medium having computer program instructions stored therein, the computer program instructions when executed by a processor, cause the processor to:

identify a taxonomy comprising a plurality of classifications;

store (a) a first record for a first provider in a datastore, wherein the first record comprises a data field with a first assigned taxonomy-based classification for the first provider from the plurality of classifications in the taxonomy, (b) a second record for a second provider in the datastore, wherein the second record comprises a data field with a second assigned taxonomy-based classification for the second provider from the plurality of classifications in the taxonomy, and (c) a third record for a third provider in the datastore, wherein the third record comprises a data field with a third assigned taxonomy-based classification for the third provider from the plurality of classifications in the taxonomy, wherein the first assigned taxonomy-based classification for the first provider is selected from a group consisting of null, empty, unknown, and not populated;

generate, by one or more machine learning models, (a) for a first claim for the first provider and based at least in part on first claim data, a first plurality of predicted taxonomy-based classification scores, wherein the first plurality of predicted taxonomy-based classification scores comprises a predicted taxonomy-based classification score for each classification in the taxonomy, (b) for a second claim for the second provider and based at least in part on second claim data, a second plurality of predicted taxonomy-based classification scores, wherein the second plurality of predicted taxonomy-based classification scores comprises a predicted taxonomy-based classification score for each classification in the taxonomy, and (c) for a third claim for the third provider and based at least in part on third claim data, a third plurality of predicted taxonomy-based classification scores, wherein the third plurality of predicted taxonomy-based classification scores comprises a predicted taxonomy-based classification score for each classification in the taxonomy;

programmatically identify (a) a first predicted taxonomy-based classification for the first claim from the first plurality of predicted taxonomy-based classification scores, (b) a second predicted taxonomy-based classification for the second claim from the second plurality of predicted taxonomy-based classification scores, and (c) a third predicted taxonomy-based classification for the third claim from the third plurality of predicted taxonomy-based classification scores, wherein (i) the second predicted taxonomy-based classification for the second claim is equivalent to the second assigned taxonomy-based classification for the second provider, and (ii) the third predicted taxonomy-based classification for the third claim is not equivalent to the third assigned taxonomy-based classification for the third provider;

programmatically compare (a) the first predicted taxonomy-based classification for the first provider with the first assigned taxonomy-based classification for the first provider, (b) the second predicted taxonomy-based classification for the second provider with the second assigned taxonomy-based classification for the second provider, and (c) the third predicted taxonomy-based classification for the third provider with the third assigned taxonomy-based classification for the third provider;

responsive to the respective comparisons, programmatically assign (a) an unknown condition to the first claim, (b) a match condition to the second claim, and (c) a not matched condition to the third claim, wherein (i) the unknown condition is assigned to any claim whose corresponding assigned taxonomy-based classification is selected from the group consisting of null, empty, unknown, and not populated, (ii) the match condition is assigned to any claim whose corresponding assigned taxonomy-based classification and respective predicted taxonomy-based classification are equivalent, and (iii) the not matched condition is assigned to any claim whose corresponding assigned taxonomy-based classification and respective predicted taxonomy-based classification are not equivalent; and responsive to assigning the unknown condition to the first claim, programmatically update the data field of the first record with the first assigned taxonomy-based classification to the first predicted taxonomy-based classification.

8. The computer program product of claim 7, wherein the computer program instructions, when executed by the processor, cause the processor to, responsive to assigning the match condition to the second claim, programmatically assign the second claim to an electronic bypass queue.

9. The computer program product of claim 8, wherein the computer program instructions, when executed by the processor, cause the processor to update a user interface to indicate assignment of the second claim to the electronic bypass queue.

10. The computer program product of claim 7, wherein the computer program instructions, when executed by the processor, cause the processor to, responsive to assigning the not matched condition to the third claim, programmatically assign the third claim to an electronic review queue.

11. The computer program product of claim 10, wherein the computer program instructions, when executed by the processor, cause the processor to update a user interface to indicate assignment of the third claim to the electronic review queue, wherein updating the user interface comprises generating a notification.

12. The computer program product of claim 7, wherein the computer program instructions, when executed by the processor, cause the processor to automatically reassign a fourth claim assigned to an electronic review queue to a standard queue.

13. A computing system comprising a non-transitory computer readable storage medium and one or more processors, the computing system configured to:

identify a taxonomy comprising a plurality of classifications;

store (a) a first record for a first provider in a datastore, wherein the first record comprises a data field with a first assigned taxonomy-based classification for the first provider from the plurality of classifications in the taxonomy, (b) a second record for a second provider in the datastore, wherein the second record comprises a data field with a second assigned taxonomy-based classification for the second provider from the plurality of classifications in the taxonomy, and (c) a third record for a third provider in the datastore, wherein the third record comprises a data field with a third assigned taxonomy-based classification for the third provider from the plurality of classifications in the taxonomy, wherein the first assigned taxonomy-based classification for the first provider is selected from a group consisting of null, empty, unknown, and not populated;

generate, by one or more machine learning models, (a) for a first claim for the first provider and based at least in part on first claim data, a first plurality of predicted taxonomy-based classification scores, wherein the first plurality of predicted taxonomy-based classification scores comprises a predicted taxonomy-based classification score for each classification in the taxonomy, (b) for a second claim for the second provider and based at least in part on second claim data, a second plurality of predicted taxonomy-based classification scores, wherein the second plurality of predicted taxonomy-based classification scores comprises a predicted taxonomy-based classification score for each classification in the taxonomy, and (c) for a third claim for the third provider and based at least in part on third claim data, a third plurality of predicted taxonomy-based classification scores, wherein the third plurality of predicted taxonomy-based classification scores comprises a predicted taxonomy-based classification score for each classification in the taxonomy;

programmatically identify (a) a first predicted taxonomy-based classification for the first claim from the first plurality of predicted taxonomy-based classification scores, (b) a second predicted taxonomy-based classification for the second claim from the second plurality of predicted taxonomy-based classification scores, and (c) a third predicted taxonomy-based classification for the third claim from the third plurality of predicted taxonomy-based classification scores, wherein (i) the second predicted taxonomy-based classification for the second claim is equivalent to the second assigned taxonomy-based classification for the second provider, and (ii) the third predicted taxonomy-based classification for the third claim is not equivalent to the third assigned taxonomy-based classification for the third provider;

programmatically compare (a) the first predicted taxonomy-based classification for the first provider with the first assigned taxonomy-based classification for the first provider, (b) the second predicted taxonomy-based classification for the second provider with the second assigned taxonomy-based classification for the second provider, and (c) the third predicted taxonomy-based classification for the third provider with the third assigned taxonomy-based classification for the third provider;

responsive to the respective comparisons, programmatically assign (a) an unknown condition to the first claim, (b) a match condition to the second claim, and (c) a not matched condition to the third claim, wherein the (i) unknown condition is assigned to any claim whose corresponding assigned taxonomy-based classification is selected from the group consisting of null, empty, unknown, and not populated, (ii) the match condition is assigned to any claim whose corresponding assigned taxonomy-based classification and respective predicted taxonomy-based classification are equivalent, and (iii) the not matched condition is assigned to any claim whose corresponding assigned taxonomy-based classification and respective predicted taxonomy-based classification are not equivalent; and responsive to assigning the unknown condition to the first claim, programmatically update the data field of the first record with the first assigned taxonomy-based classification to the first predicted taxonomy-based classification.

14. The computing system of claim 13, wherein the computing system is further configured to, responsive to assigning the match condition to the second claim, programmatically assign the second claim to an electronic bypass queue.

15. The computing system of claim 14, wherein the computing system is further configured to update a user interface to indicate assignment of the second claim to the electronic bypass queue.

16. The computing system of claim 13, wherein the computing system is further configured to, responsive to assigning the not matched condition to the third claim, programmatically assign the third claim to an electronic review queue.

17. The computing system of claim 16, wherein the computing system is further configured to update a user interface to indicate assignment of the third claim to the electronic review queue, wherein updating the user interface comprises generating a notification.

18. The computing system of claim 13, wherein the computing system is further configured to automatically reassign a fourth claim assigned to an electronic review queue to a standard queue.

\* \* \* \* \*

UNITED STATES PATENT AND TRADEMARK OFFICE
CERTIFICATE OF CORRECTION

PATENT NO. : 11,581,073 B2  
APPLICATION NO. : 16/677990  
DATED : February 14, 2023  
INVENTOR(S) : Lorcan B. Mac Manus et al.

Page 1 of 1

It is certified that error appears in the above-identified patent and that said Letters Patent is hereby corrected as shown below:

On the Title Page

In Column 1, item (12), Line 2, delete "MacManus" and insert -- Mac Manus --, therefor.

In Column 1, item (72), Line 1, delete "MacManus," and insert -- Mac Manus, --, therefor.

In the Claims

In Column 23, Claim 1, Line 53, delete "respected" and insert -- respective --, therefor.

In Column 26, Claim 13, Line 66, delete "wherein the (i)" and insert -- wherein (i) the --, therefor.

Signed and Sealed this  
Twenty-seventh Day of June, 2023

Katherine Kelly Vidal  
*Director of the United States Patent and Trademark Office*